(12) United States Patent
Liang et al.

(10) Patent No.: US 9,758,486 B1
(45) Date of Patent: Sep. 12, 2017

(54) EDARAVONE-GOSSYPOL DERIVATIVES WITH ANTITUMOR ACTIVITIES AND A METHOD OF PREPARING THE SAME

(71) Applicants: Chengyuan Liang, Xi'an (CN); Danni Tian, Xi'an (CN); Minyi Jia, Xi'an (CN); Xiaolin Xie, Xi'an (CN); Dezhu Zhang, Xi'an (CN); Weihui Ju, Xi'an (CN); Shunjun Ding, Xi'an (CN); Xuechuan Wang, Xi'an (CN)

(72) Inventors: Chengyuan Liang, Xi'an (CN); Danni Tian, Xi'an (CN); Minyi Jia, Xi'an (CN); Xiaolin Xie, Xi'an (CN); Dezhu Zhang, Xi'an (CN); Weihui Ju, Xi'an (CN); Shunjun Ding, Xi'an (CN); Xuechuan Wang, Xi'an (CN)

(73) Assignee: SHAANXI UNIVERSITY OF SCIENCE AND TECHNOLOGY, Xi'an (CN)

(*) Notice: Subject to any disclaimer, the term of this patent is extended or adjusted under 35 U.S.C. 154(b) by 0 days.

(21) Appl. No.: 15/489,713

(22) Filed: Apr. 17, 2017

(30) Foreign Application Priority Data

Mar. 27, 2017 (CN) .......................... 2017 1 0185860

(51) Int. Cl.
  *C07D 231/36* (2006.01)
  *C07D 231/22* (2006.01)
  *C07D 231/26* (2006.01)

(52) U.S. Cl.
  CPC ......... *C07D 231/36* (2013.01); *C07D 231/22* (2013.01); *C07D 231/26* (2013.01)

(58) Field of Classification Search
  None
  See application file for complete search history.

(56) References Cited

U.S. PATENT DOCUMENTS 9,125,899 B1 * 9/2015 Ness .................... A61K 31/415
9,642,835 B2 * 5/2017 Wandinger-Ness .. A61K 31/403

* cited by examiner

*Primary Examiner* — Kamal Saeed

(57) ABSTRACT

A compound with antitumor activities represented by formula I:

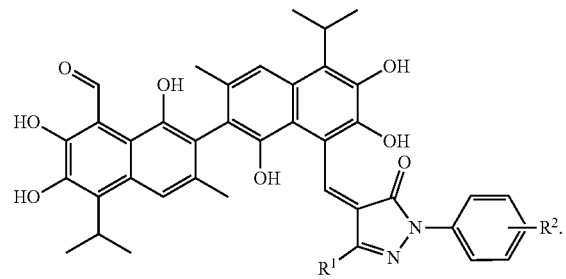

In formula I, $R_1$ is alkyl, alkoxy, or ethenyl; and $R_2$ is alkyl, alkoxy, or halogen.

10 Claims, No Drawings

EDARAVONE-GOSSYPOL DERIVATIVES WITH ANTITUMOR ACTIVITIES AND A METHOD OF PREPARING THE SAME

The present invention claims priority to Chinese Patent Application No. 201710185860.0, filed on Mar. 27, 2017, which is incorporated by reference for all purposes as if fully set forth herein.

BACKGROUND OF THE INVENTION

Field of the Invention

The present invention relates to the field of pharmaceutical chemistry, and in particular, to edaravone-gossypol derivatives with antitumor activities of and a method of preparing the same.

Discussion of the Related Art

Edaravone is a potent free radical scavenger with low molecular weight, high lipophilicity, and easy to reach biological target. It was approved and marketed in Japan in 2001 for cerebral hemorrhage, cerebral edema, and cerebral infarction treatment. Its free radical scavenging function and antioxidant effect has been confirmed and also used in adjuvant therapy for cancer patients in chemotherapy. Recent studies have shown that edaravone's mechanism of action involves many aspects, and its clinical application is not limited to ischemic stroke, extending to the field outside the nervous system. First, edaravone can inhibit xanthine oxidation enzyme and hypoxanthine oxidase activities, and stimulate cells to produce prostacyclin, reduce the release of leukotrienes, exhibit anti-tumor effect, and create synergies with radiotherapy and chemotherapy. Second, edaravone can directly remove hydroxyl groups, effectively inhibit the generation of lipid free radicals, and block the development of tumor by successfully inhibiting irreversible damage effect caused by the free radicals mediated by protein nucleic acid. Third, edaravone can inhibit the expression of aquaporin-4, and thus reduce edema associated with tumor. Edaravone has broad application and clinical value.

Gossypol is a polyphenolic bis-naphthalene aldehyde compound, and a natural yellow pigment found in small cell glands between cotton cells. Its structure was determined in 1938. Gossypol is recognized as an effective male contraceptive agent, but at the same time it also has large toxicity. The two aldehydes in its molecule not only play a role in tautomerization but also increase its chemical activities. They may contribute to its toxicity. As a new natural product with potential, in the early 1960s, the antitumor activity of gossypol was confirmed. Studies have shown that the antitumor mechanism of gossypol relates to its ability to inhibit the activation of topoisomerase II and the stability of topoisomerase-DNA complex formation, affecting cell functions. Gossypol also activates the expression of TGF-β1 in prostate cancer cell line PC3, and inhibits cell DNA synthesis and terminates cells in G0/G1 phase. In view of its antitumor activities, in recent years, the study of anti-tumor mechanism of gossypol has become active.

The present invention utilizes the aldehyde group of gossypol and the active site in the edaravone structure to synthesize edaravone-gossypol derivatives to achieve better anti-tumor activities and lower toxicities.

SUMMARY OF THE INVENTION

In one embodiment, the present invention provides a compound with antitumor activities represented by formula I:

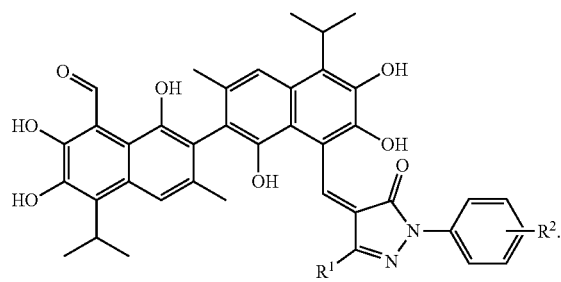

In formula I, $R_1$ is alkyl, alkoxy, or ethenyl; and $R_2$ is alkyl, alkoxy, or halogen.

In another embodiment, the compound is:

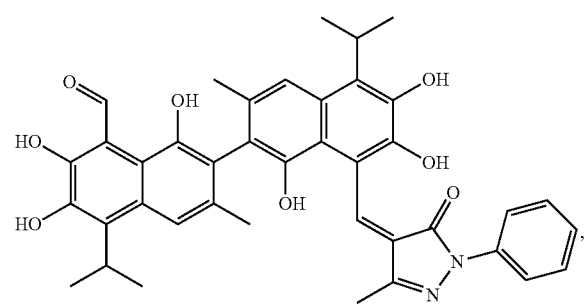

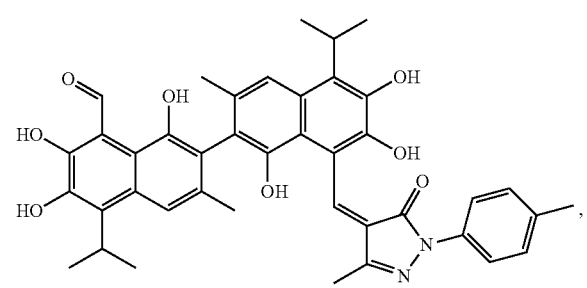

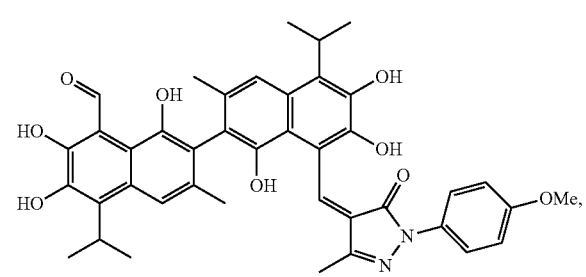

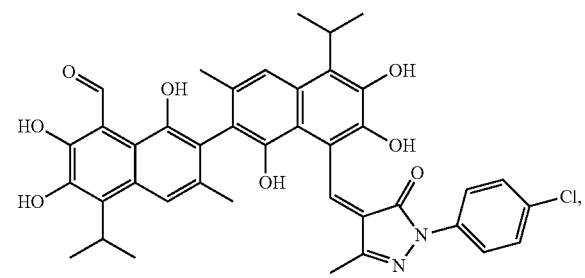

E
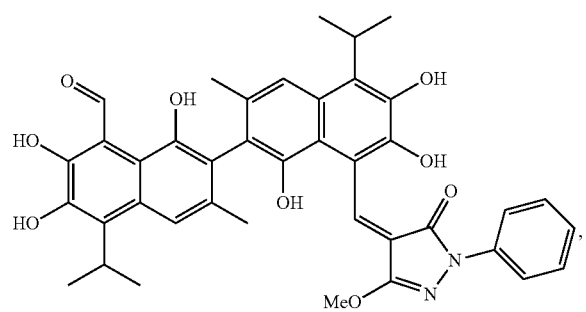
F
J
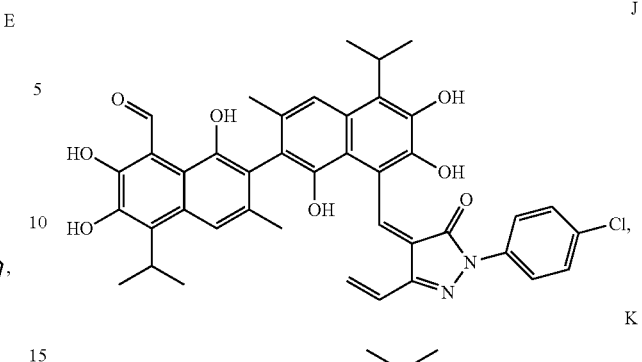
K
G
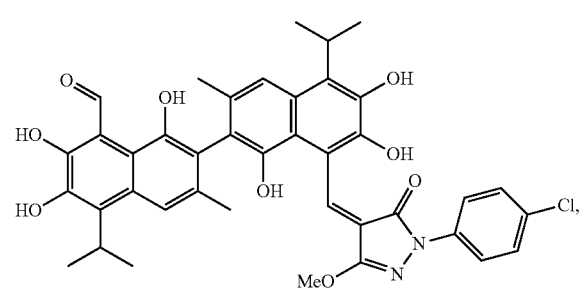
or
L
H
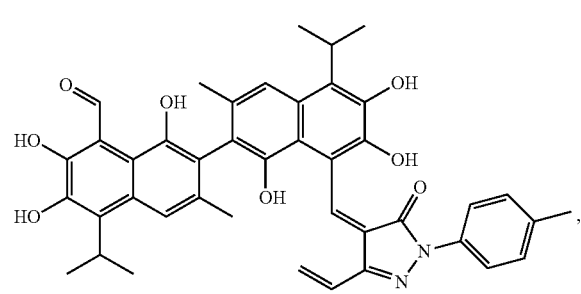
In one embodiment, the present invention provides a method of preparing the compound of formula I. The method includes reacting a compound of formula A with a compound of formula B in an organic acid with ammonium acetate as a catalyst to obtain the compound of formula I.
A
I
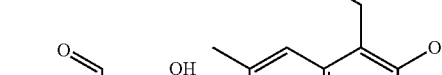
B

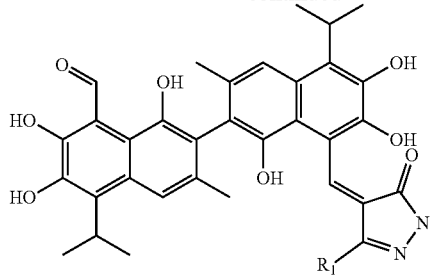

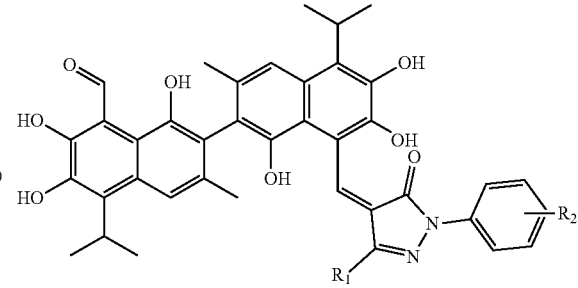

In another embodiment, the compound of formula A and the compound of formula B are heated at 40-80° C. for 2-5 hours.

In another embodiment, the compound of formula A and the compound of formula B are heated at 40-50° C. for 3 hours.

In another embodiment, the method of preparing the compound of formula I includes recrystallizing the compound of formula I in methanol or ethyl acetate.

In another embodiment, the organic acid is formic acid or acetic acid.

In another embodiment, a molar ratio of the compound B and the compound A is 1:1 to 1:1.5.

In another embodiment, the molar ratio of the compound B and the compound A is 1:1.2

In one embodiment, the present invention provides a method of using the compound of formula I 1 in antitumor drug research, development, and application.

It is to be understood that both the foregoing general description and the following detailed description are exemplary and explanatory and are intended to provide further explanation of the invention as claimed.

In formula I, $R_1$ is alkyl, alkoxy, or ethenyl; and $R_2$ is alkyl, alkoxy, or halogen.

More preferably, the compounds have the following formulas.

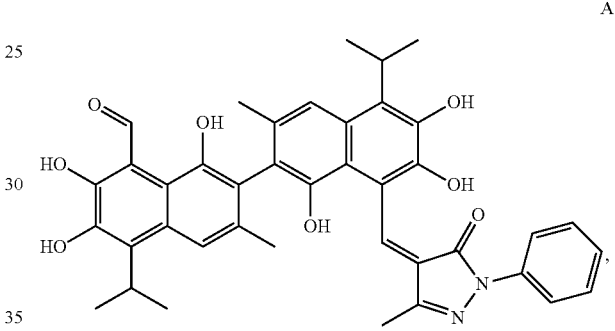

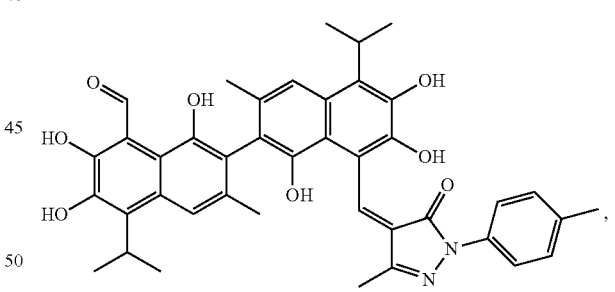

DETAILED DESCRIPTION OF THE ILLUSTRATED EMBODIMENTS

Reference will now be made in detail to embodiments of the present invention.

As used herein, the term alkyl refers to a monovalent straight or branched chain, saturated aliphatic hydrocarbon radical having 1-8 carbon atoms. For example, alkyl refers to any of the hexyl alkyl and pentyl alkyl isomers as well as n-, iso-, sec- and t-butyl, n- and iso-propyl, ethyl, or methyl. The alkoxy refers to an alkyl ether group wherein the alkyl moiety is as defined above.

Alkyl and alkoxy also include saturated aliphatic hydrocarbon radicals wherein one or more hydrogens are replaced with deuterium, for example, $CD_3$.

The term halogen refers to fluorine, chlorine, bromine and iodine.

The present invention provides edaravone-gossypol derivatives with antitumor activities and a method of preparing the same.

The structures of the edaravone-gossypol derivatives (hereafter, compounds) of the present invention are represented by formula I:

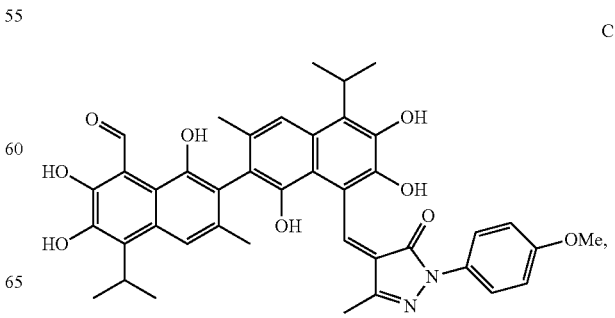

D
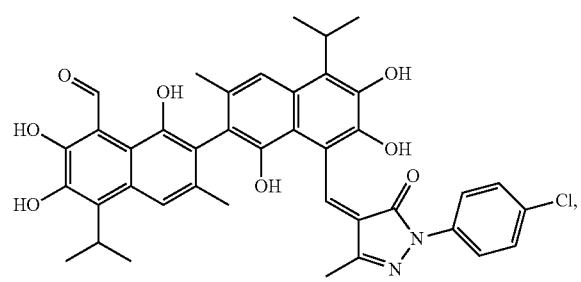
E
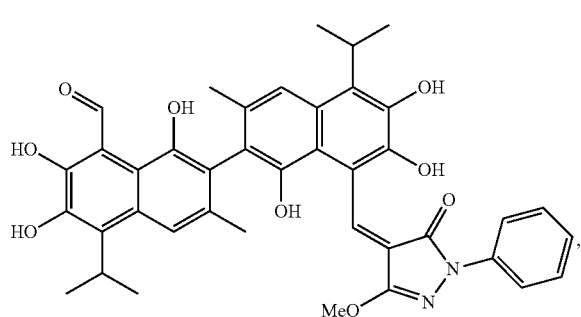
F
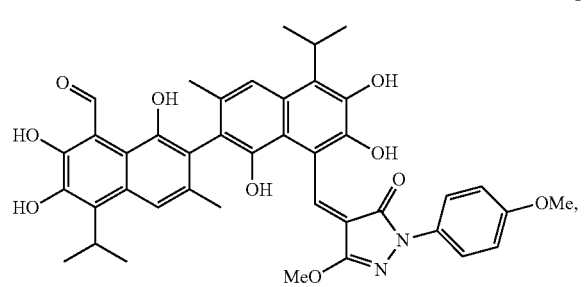
G
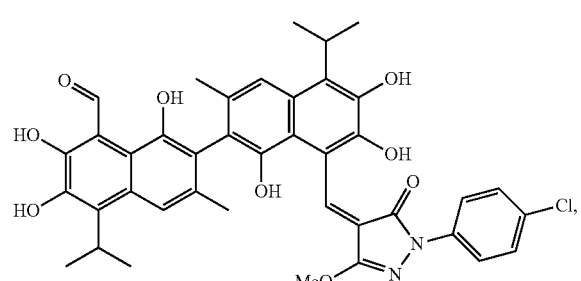
H
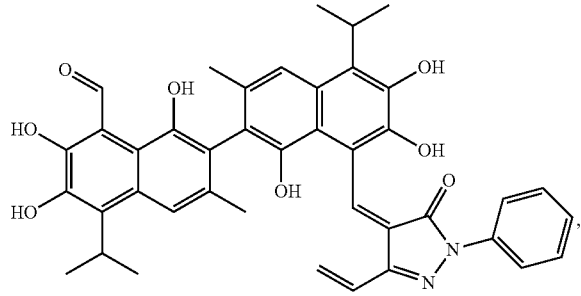
I
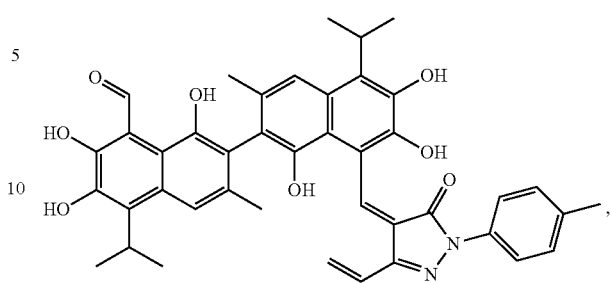
J
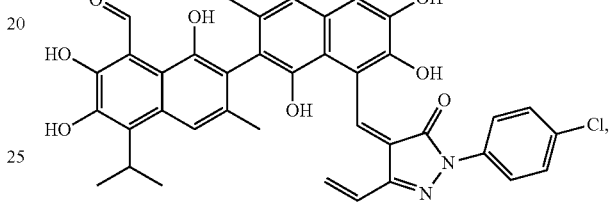
K
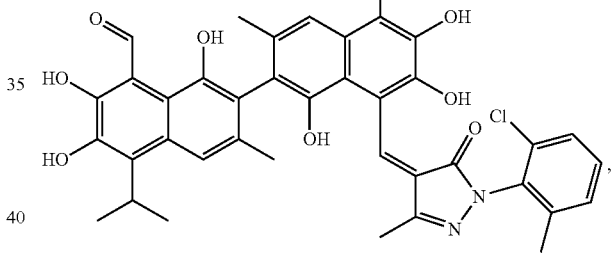
or
L
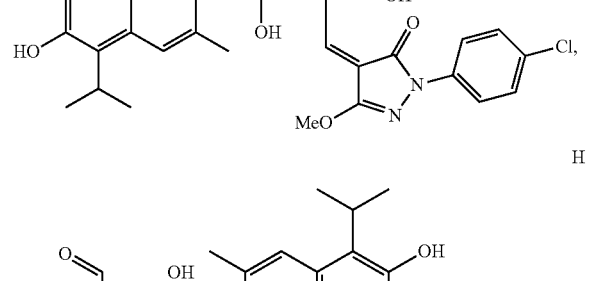
The present invention also provides a method of preparing the above-described compounds.
The above-described compounds are obtained by using gossypol (compound of formula B) and edaravone and its derivatives (compound of formula A) as starting materials, an organic acid as reaction medium and ammonium acetate as a catalyst under heating.

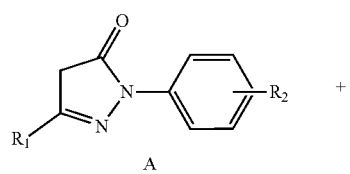

A

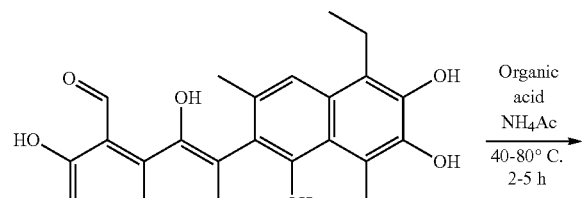

B

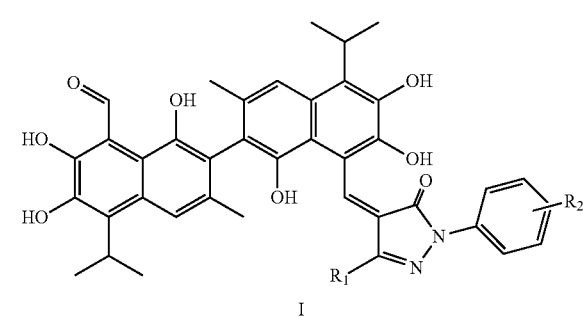

I

In the formulas above, $R_1$ and $R_2$ have the same definitions as above.

The synthesis route includes the following steps.

(1) Gossypol was placed in a three-necked flask, and dissolved in an organic acid. A catalyst, 0.1 equivalent amount of ammonium acetate (based on the amount of gossypol), was added to the gossypol solution in the flask. 1 to 1.5 equivalents of edaravone or its derivatives were slowly added to the flask. The mixture was then heated to 40-80° C. for 2-5 h;

(2) When thin layer chromatography (TLC) indicates that the reaction is complete, stop the reaction and concentrate the reaction mixture under reduced pressure. A small amount of water was added to the concentrated reaction mixture, and the mixture was then allowed to stand overnight for crystallization. The mixture was then filtered and washed with sodium bicarbonate solution to obtain a crude product.

(3) The crude product was recrystallized from methanol or ethyl acetate to give the target compound.

The organic acid in step (1) is acetic acid or formic acid. Preferably, the organic acid is acetic acid.

A molar ratio of gossypol to edaravone or its derivatives in step (1) is from 1:1 to 1:1.5. Preferably, the molar ratio is 1:1.2.

The reaction temperature in step (1) is 40 to 80° C. Preferably, the reaction temperature is 40° C. to 50° C.

The reaction time in step (1) is 2 to 5 hours (h). Preferably, the reaction time is 3 h.

The invention has the advantages that the starting materials are readily available, the reaction condition is mild and safe, and the conversion rate and yield are high. The synthetic route is suitable for industrial production.

INVENTIVE EXAMPLES

The invention will now be further elucidated with reference to specific embodiments. These examples are for illustrative purposes only and are not intended to limit the scope and spirit of the invention.

Example 1

The preparation of compound A (Z)-1,1',6,6',7,7'-hexahydroxy-5,5'-diisopropyl-3,3'-dimethyl-8'-((3-methyl-5-oxo-1-phenyl-1H-pyrazol-4(5H)-ylidene)methyl)-[2,2'-binaphthalene]-8-carbaldehyde:

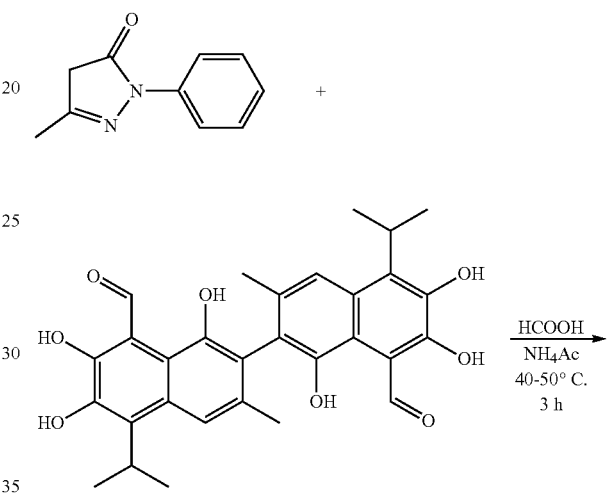

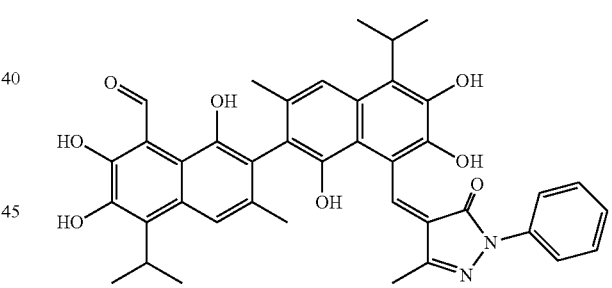

103.71 mg (0.2 mmol) of gossypol were dissolved in 25 mL of formic acid in a 50 ml three-necked flask. 1.54 mg (0.02 mmol) of ammonium acetate was added to the gossypol solution under stirring and heating. 41.81 mg (0.24 mmol) of edaravone in 5 mL acetic acid was slowly added to the mixture in the three-necked flask under stirring. The mixture was then heated to 40-50° C. for 3 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound A. The crude product was recrystallized from methanol and dried to obtain 87.72 mg (0.13 mmol) of compound A. The overall yield is 64.50%.

Compound A

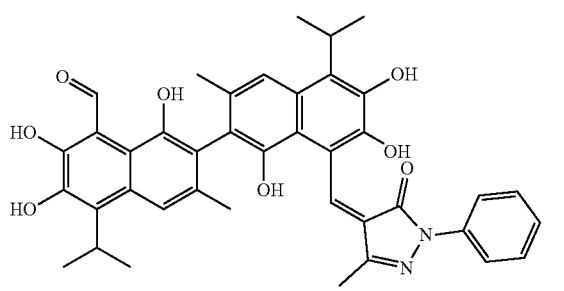

¹H-NMR (400 MHz, DMSO-d₆) δ (ppm): 11.21 (1H, s), 9.05 (3H, s), 7.96 (2H, d, J=1.5 Hz), 7.72 (1H, s), 7.09-7.56 (5H, m, J=7.5 Hz, 1.5 Hz), 5.83 (3H, s), 2.72 (2H, m, J=6.8 Hz), 2.26 (6H, s), 2.04 (3H, s), 1.47 (12H, d, J=6.8 Hz); ¹³C-NMR (101 MHz, DMSO-d₆) δ (ppm): 191.2, 171.5, 155.6, 154.5, 146.6, 142.3, 139.3, 134.1, 132.0, 128.1, 127.0, 117.3, 114.3, 102.9, 55.3, 30.8, 25.3, 20.0, 12.1; MS (ESI) for (M+H)⁺: 675.3.

Example 2

The preparation of compound B (Z)-1,1',6,6',7,7'-hexahydroxy-5,5'-diisopropyl-3,3'-dimethyl-8'-((3-methyl-5-oxo-1-(p-tolyl)-1H-pyrazol-4(5H)-ylidene)methyl)-[2,2'-binaphthalene]-8-carbaldehyde:

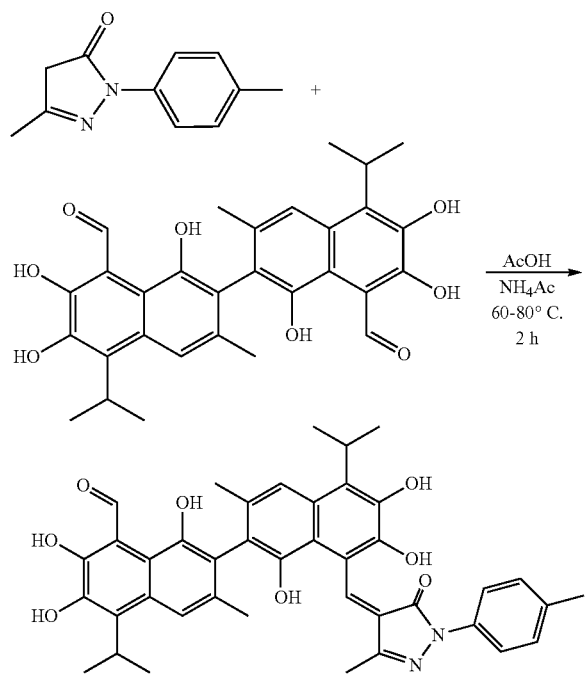

103.71 mg (0.2 mmol) of gossypol were dissolved in 25 mL of acetic acid in a 50 ml three-necked flask. 1.54 mg (0.02 mmol) of ammonium acetate was added to the gossypol solution under stirring and heating. 45.18 mg (0.24 mmol) of 3-methyl-1-(p-tolyl)-1H-pyrazole-5-one in 5 mL acetic acid was slowly added to the mixture in the three-necked flask under stirring. The mixture was then heated to 60-80° C. for 2 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound B. The crude product was recrystallized from methanol and dried to obtain 90.91 mg (0.132 mmol) of compound B. The overall yield is 66.10%.

Compound B

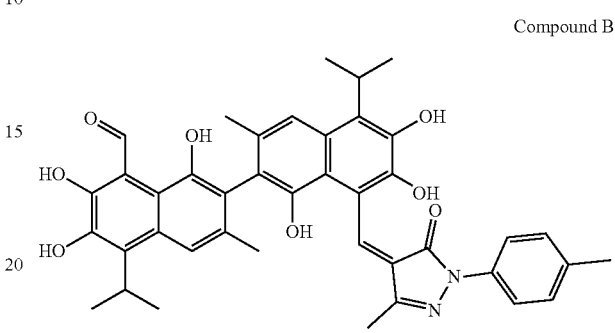

¹H-NMR (400 MHz, DMSO-d₆) δ (ppm): 11.21 (1H, s), 8.95 (3H, s), 7.83 (2H, d, J=1.5 Hz), 7.71 (1H, s), 6.94-7.49 (4H, m, J=7.5 Hz, 1.5 Hz), 5.82 (3H, s), 2.72 (2H, m, J=6.8 Hz), 2.31 (6H, s), 2.14 (3H, s), 1.62 (3H, s), 1.34 (12H, d, J=6.8 Hz); ¹³C-NMR (101 MHz, DMSO-d₆) δ (ppm): 191.1, 170.3, 155.8, 154.2, 145.6, 141.3, 138.3, 134.7, 132.4, 128.3, 127.0, 117.3, 114.3, 101.9, 56.3, 32.8, 27.3, 22.4, 20.6, 13.2; MS (ESI) for (M+H)⁺: 689.3.

Example 3

The preparation of compound C (Z)-1,1',6,6',7,7'-hexahydroxy-5,5'-diisopropyl-3,3'-dimethyl-8'-((3-methyl-5-oxo-1-(p-tolyl)-1H-pyrazol-4(5H)-ylidene)methyl)-[2,2'-binaphthalene]-8-carbaldehyde:

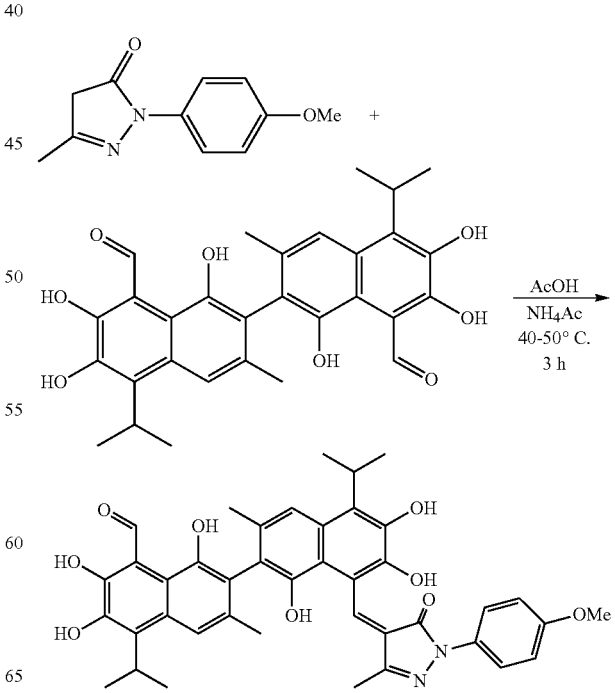

103.71 mg (0.2 mmol) of gossypol were dissolved in 25 mL of acetic acid in a 50 ml three-necked flask. 1.54 mg (0.02 mmol) of ammonium acetate was added to the gossypol solution under stirring and heating. 49.02 mg (0.24 mmol) of 1-(4-methoxyphenyl)-3-methyl-1H-pyrazole-5-one in 8 mL acetic acid was slowly added to the mixture in the three-necked flask under stirring. The mixture was then heated to 40-50° C. for 3 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound C. The crude product was recrystallized from ethyl acetate and dried to obtain 112.76 mg (0.16 mmol) of compound C. The overall yield is 80.00%.

Compound C

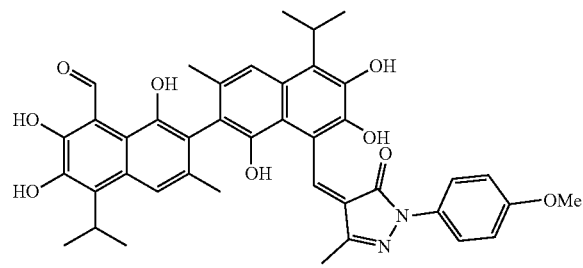

$^1$H-NMR (400 MHz, DMSO-d$_6$) δ (ppm): 11.21 (1H, s), 9.05 (3H, s), 7.80 (2H, d, J=1.5 Hz), 7.68 (1H, s), 6.92-7.41 (4H, m, J=7.5 Hz, 1.5 Hz), 5.82 (3H, s), 3.52 (3H, s), 2.72 (2H, m, J=6.8 Hz), 2.31 (6H, s), 2.06 (3H, s), 1.41 (12H, d, J=6.8 Hz); $^{13}$C-NMR (101 MHz, DMSO-d$_6$) δ (ppm): 192.2, 163.5, 152.0, 148.5, 146.8, 144.3, 141.6, 136.3, 135.8, 134.1, 133.3, 132.0, 128.5, 127.2, 126.0, 118.7, 116.8, 115.9, 100.9, 57.3, 34.8, 27.6, 24.3, 22.3, 16.1; MS (ESI) for (M+H)$^+$: 705.3.

Example 4

The preparation of compound D (Z)-8'-((1-(4-chlorophenyl)-3-methyl-5-oxo-1H-pyrazol-4(5H)-ylidene)methyl)-1,1',6,6',7,7'-hexahydroxy-5,5'-diisopropyl-3,3'-dimethyl-[2,2'-binaphthalene]-8-carbaldehyde:

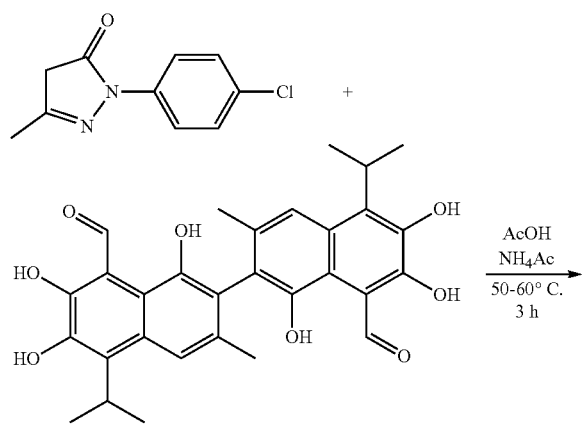

103.71 mg (0.2 mmol) of gossypol were dissolved in 25 mL of acetic acid in a 50 ml three-necked flask. 1.54 mg (0.02 mmol) of ammonium acetate was added to the gossypol solution under stirring and heating. 50.07 mg (0.24 mmol) of 1-(4-chlorophenyl)-3-methyl-1H-pyrazole-5-one in 8 mL acetic acid was slowly added to the mixture in the three-necked flask under stirring. The mixture was then heated to 50-60° C. for 3 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound D. The crude product was recrystallized from ethyl acetate and dried to obtain 99.29 mg (0.14 mmol) of compound D. The overall yield is 70.00%.

Compound D

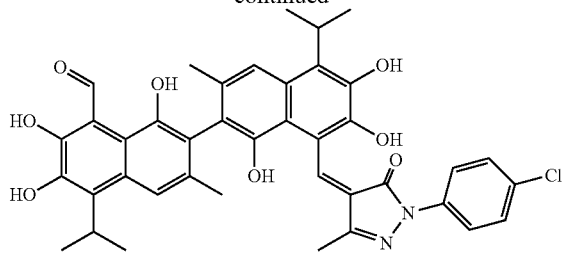

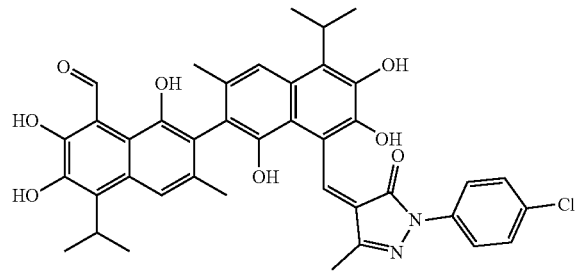

$^1$H-NMR (400 MHz, DMSO-d$_6$) δ (ppm): 11.21 (1H, s), 9.04 (3H, s), 8.03 (2H, d, J=1.5 Hz), 7.68 (1H, s), 7.12-7.83 (4H, m, J=7.5 Hz, 1.5 Hz), 5.84 (3H, s), 2.83 (2H, m, J=6.8 Hz), 2.27 (6H, s), 2.16 (3H, s), 1.44 (12H, d, J=6.8 Hz); $^{13}$C-NMR (101 MHz, DMSO-d$_6$) δ (ppm): 194.1, 165.7, 154.2, 150.1, 148.4, 144.0, 142.3, 139.1, 134.9, 132.7, 131.3, 130.3, 128.6, 127.1, 118.2, 116.2, 115.8, 113.7, 112.2, 110.6, 28.3, 25.1, 17.2; MS (ESI) for (M+H)$^+$: 709.2.

Example 5

The preparation of compound E (Z)-1,1',6,6',7,7'-hexahydroxy-5,5'-diisopropyl-8'-((3-methoxy-5-oxo-1-phenyl-1H-pyrazol-4(5H)-ylidene)methyl)-3,3'-dimethyl-[2,2'-binaphthalene]-8-carbaldehyde:

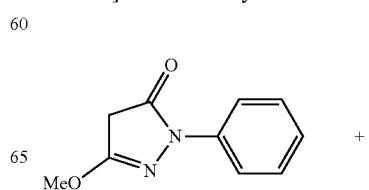

15
-continued

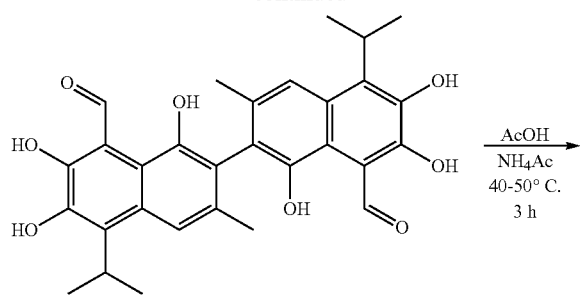

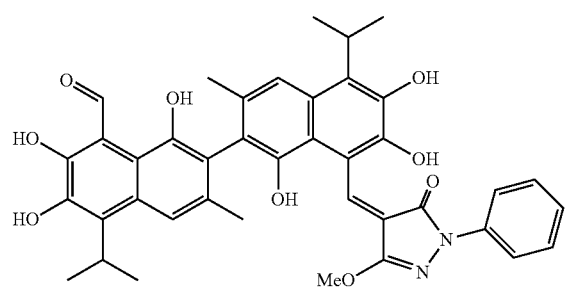

103.71 mg (0.2 mmol) of gossypol were dissolved in 25 mL of acetic acid in a 50 ml three-necked flask. 1.54 mg (0.02 mmol) of ammonium acetate was added to the gossypol solution under stirring and heating. 45.65 mg (0.24 mmol) of 1-phenyl-3-methxoy-1H-pyrazole-5-one in 5 mL acetic acid was slowly added to the mixture in the three-necked flask under stirring. The mixture was then heated to 40-50° C. for 3 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound E. The crude product was recrystallized from ethyl acetate and dried to obtain 116.04 mg (0.168 mmol) of compound E. The overall yield is 84.00%.

Compound E

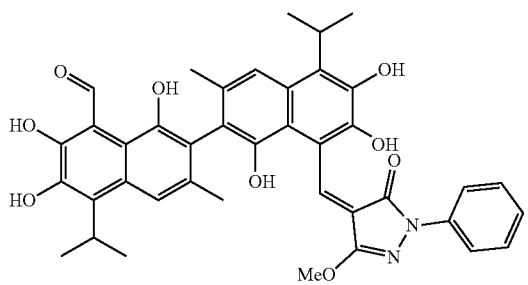

$^1$H-NMR (400 MHz, DMSO-$d_6$) δ (ppm): 11.21 (1H, s), 9.05 (3H, s), 7.66 (2H, d, J=1.5 Hz), 7.72 (1H, s), 6.88-7.36 (5H, m, J=7.5 Hz, 1.5 Hz), 5.83 (3H, s), 2.74 (2H, m, J=6.8 Hz), 2.30 (6H, s), 2.08 (3H, s), 1.57 (12H, d, J=6.8 Hz); $^{13}$C-NMR (101 MHz, DMSO-$d_6$) δ (ppm): 191.2, 171.9, 155.5, 154.6, 146.8, 139.5, 133.1, 131.0, 129.1, 127.0, 118.3, 115.3, 103.9, 57.3, 31.8, 26.3, 23.0, 13.8; MS (ESI) for (M+H)$^+$: 691.3.

16

Example 6

The preparation of compound F (Z)-1,1',6,6',7,7'-hexahydroxy-5,5'-diisopropyl-8'-((3-methoxy-5-oxo-1-(p-tolyl)-1H-pyrazol-4(5H)-ylidene)methyl)-3,3'-dimethyl-[2,2'-binaphthalene]-8-carbaldehyde:

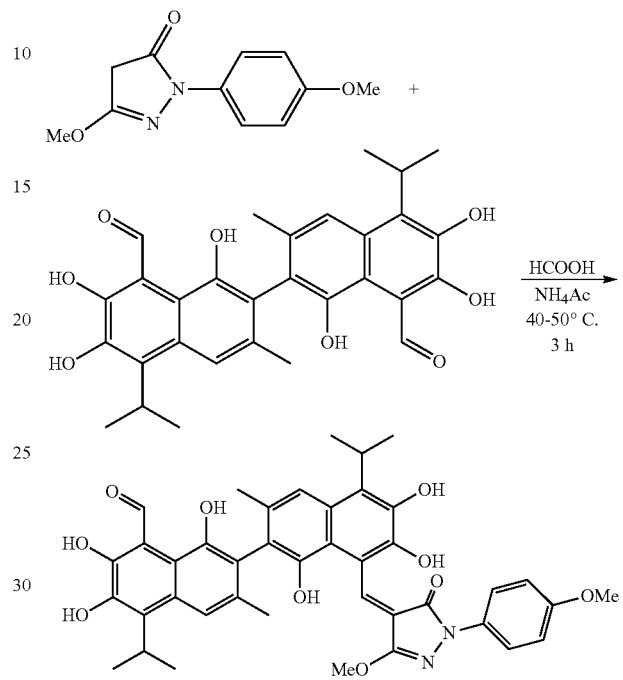

103.71 mg (0.2 mmol) of gossypol were dissolved in 25 mL of formic acid in a 50 ml three-necked flask. 1.54 mg (0.02 mmol) of ammonium acetate was added to the gossypol solution under stirring and heating. 52.85 mg (0.24 mmol) of 3-methoxy-1-(4-methoxyphenyl)-1H-pyrazole-5-one in 8 mL acetic acid was slowly added to the mixture in the three-necked flask under stirring. The mixture was then heated to 40-50° C. for 3 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound F. The crude product was recrystallized from ethyl acetate and dried to obtain 106.67 mg (0.148 mmol) of compound F. The overall yield is 74.00%.

Compound F

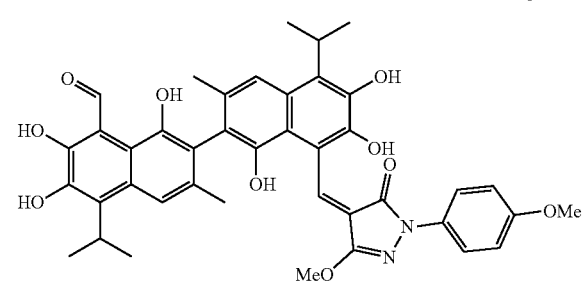

$^1$H-NMR (400 MHz, DMSO-$d_6$) δ (ppm): 11.25 (1H, s), 9.01 (3H, s), 7.91 (2H, d, J=1.5 Hz), 7.68 (1H, s), 7.02-7.36 (4H, m, J=7.5 Hz, 1.5 Hz), 5.87 (3H, s), 3.22 (3H, s), 2.70 (2H, m, J=6.8 Hz), 2.33 (6H, s), 2.02 (3H, s), 1.51 (12H, d, J=6.8 Hz); $^{13}$C-NMR (101 MHz, DMSO-$d_6$) δ (ppm): 191.4, 164.2, 153.0, 147.9, 146.7, 144.2, 141.8, 137.0, 136.1, 135.9, 134.8, 131.7, 129.0, 127.1, 126.7, 118.8, 116.2, 115.5, 99.5, 60.3, 35.8, 29.6, 23.3, 21.3, 14.8 MS (ESI) for (M+H)$^+$: 721.3.

Example 7

The preparation of compound G (Z)-8'-((1-(4-chlorophenyl)-3-methoxy-5-oxo-1H-pyrazol-4(5H)-ylidene)methyl)-1,1',6,6',7,7'-hexahydroxy-5,5'-diisopropyl-3,3'-dimethyl-[2,2'-binaphthalene]-8-carbaldehyde:

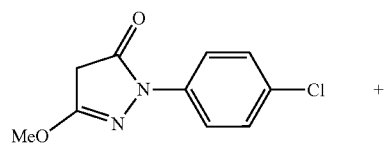

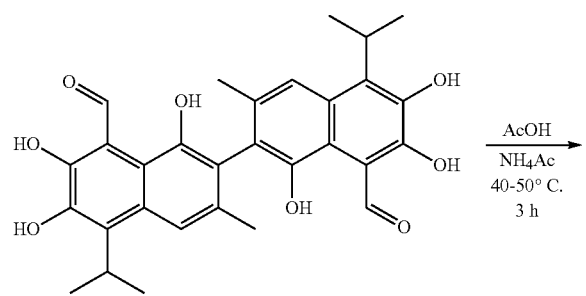

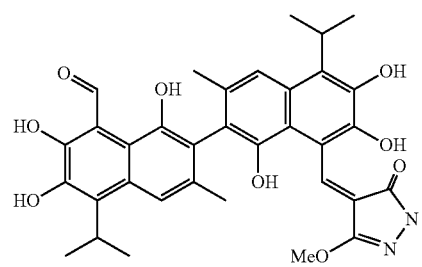

103.71 mg (0.2 mmol) of gossypol were dissolved in 25 mL of acetic acid in a 50 ml three-necked flask. 1.54 mg (0.02 mmol) of ammonium acetate was added to the gossypol solution under stirring and heating. 53.91 mg (0.24 mmol) of 1-(4-chlorophenyl)-3-methoxy-1H-pyrazole-5-one in 8 mL acetic acid was slowly added to the mixture in the three-necked flask under stirring. The mixture was then heated to 40-50° C. for 3 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound G. The crude product was recrystallized from ethyl acetate and dried to obtain 121.83 mg (0.168 mmol) of compound G. The overall yield is 84.00%.

Compound G

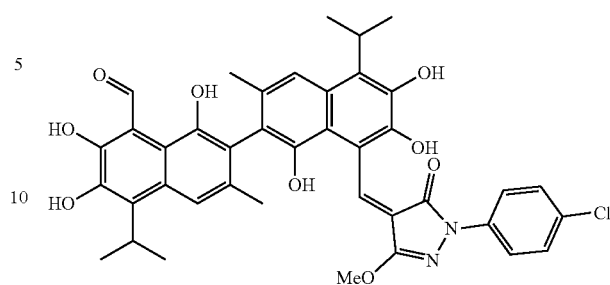

$^1$H-NMR (400 MHz, DMSO-$d_6$) δ (ppm): 11.19 (1H, s), 9.01 (3H, s), 8.05 (2H, d, J=1.5 Hz), 7.67 (1H, s), 7.22-7.73 (4H, m, J=7.5 Hz, 1.5 Hz), 5.88 (3H, s), 3.77 (3H, s), 2.73 (2H, m, J=6.8 Hz), 2.37 (6H, s), 1.49 (12H, d, J=6.8 Hz); $^{13}$C-NMR (101 MHz, DMSO-$d_6$) δ (ppm): 189.1, 165.3, 154.7, 151.1, 148.2, 144.4, 141.5, 139.5, 134.8, 132.6, 132.0, 130.5, 127.3, 126.3, 118.5, 117.0, 115.7, 113.8, 112.4, 55.6, 28.4, 25.2, 18.2; MS (ESI) for (M+H)$^+$:725.2.

Example 8

The preparation of compound H (Z)-1,1',6,6',7,7'-hexahydroxy-5,5'-diisopropyl-3,3'-dimethyl-8'-((5-oxo-1-phenyl-3-vinyl-1H-pyrazol-4(5H)-ylidene)methyl)-[2,2'-binaphthalene]-8-carbaldehyde:

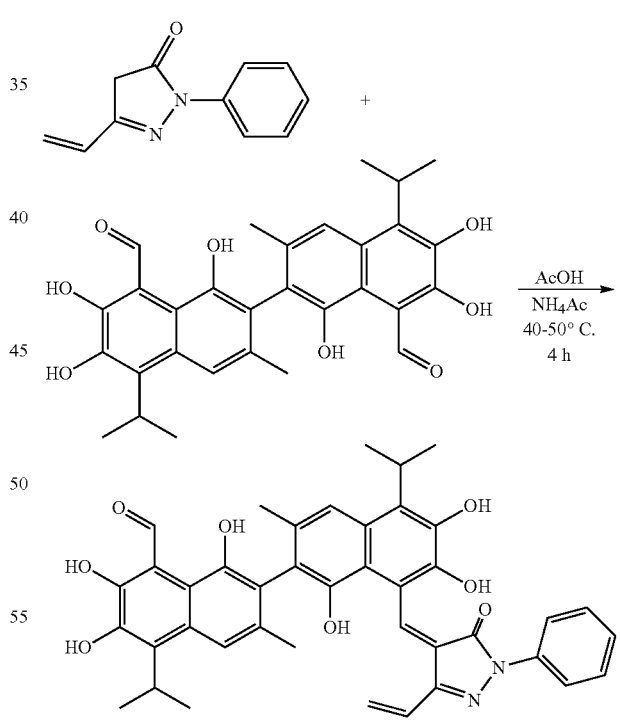

103.71 mg (0.2 mmol) of gossypol were dissolved in 25 mL of acetic acid in a 50 ml three-necked flask. 1.54 mg (0.02 mmol) of ammonium acetate was added to the gossypol solution under stirring and heating. 44.69 mg (0.24 mmol) of 1-phenyl-3-ethenyl-1H-pyrazole-5-one in 5 mL acetic acid was slowly added to the mixture in the three-necked flask under stirring. The mixture was then heated to 40-50° C. for 4 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound H. The crude product was recrystallized from ethyl acetate and dried to obtain 103.01 mg (0.15 mmol) of compound H. The overall yield is 75.00%.

Compound H

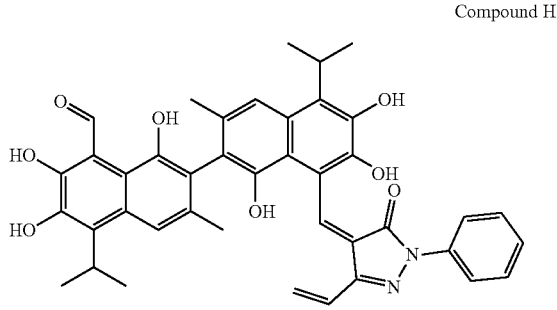 [SMILES: C=CC1=NN(c2ccccc2)C(=O)/C1=C\c1c(O)c(O)c(C(C)C)c2cc(C)c(-c3c(C)cc4c(C(C)C)c(O)c(O)c(C=O)c4c3O)c(O)c12]

$^1$H-NMR (400 MHz, DMSO-$d_6$) δ (ppm): 11.26 (1H, s), 9.07 (3H, s), 8.02 (2H, d, J=1.5 Hz), 7.82 (1H, s), 7.23-7.66 (5H, m, J=7.5 Hz, 1.5 Hz), 5.86 (3H, s), 4.99 (1H, m), 4.61 (2H, d), 2.61 (2H, m, J=6.8 Hz), 2.40 (6H, s), 1.49 (12H, d, J=6.8 Hz); $^{13}$C-NMR (101 MHz, DMSO-$d_6$) δ (ppm): 192.2, 164.5, 155.5, 154.8, 149.2, 143.1, 142.2, 141.3, 136.1, 134.1, 133.2, 130.1, 128.2, 127.1, 123.7, 119.2, 117.2, 115.3, 113.6, 112.2, 110.6, 59.2, 30.1, 24.0; MS (ESI) for (M+H)$^+$: 687.3.

Example 9

The preparation of compound I (Z)-1,1',6,6',7,7'-hexahydroxy-5,5'-diisopropyl-3,3'-dimethyl-8'-((5-oxo-1-(p-tolyl)-3-vinyl-1H-pyrazol-4(5H)-ylidene)methyl)-[2,2'-binaphthalene]-8-carbaldehyde:

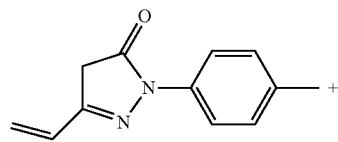

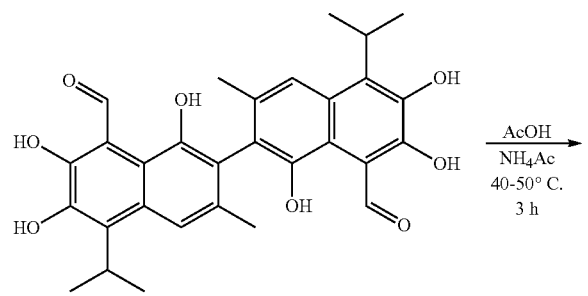

103.71 mg (0.2 mmol) of gossypol were dissolved in 25 mL of acetic acid in a 50 ml three-necked flask. 1.54 mg (0.02 mmol) of ammonium acetate was added to the gossypol solution under stirring and heating. 48.05 mg (0.24 mmol) of 1-(p-tolyl)-3-ethenyl-1H-pyrazole-5-one in 5 mL acetic acid was slowly added to the mixture in the three-necked flask under stirring. The mixture was then heated to 40-50° C. for 3 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound I. The crude product was recrystallized from ethyl acetate and dried to obtain 123.34 mg (0.176 mmol) of compound I. The overall yield is 88.00%.

Compound I

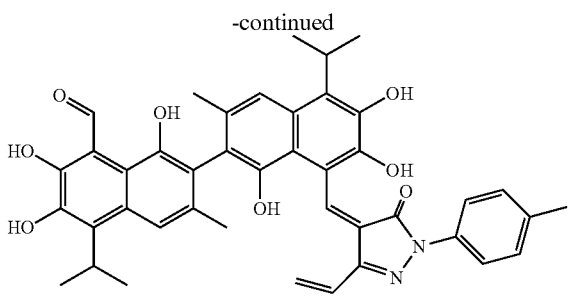

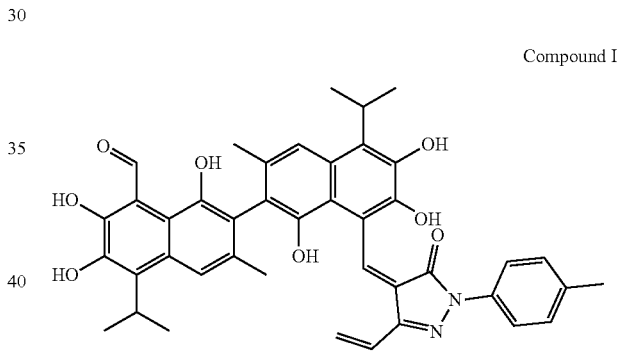

$^1$H-NMR (400 MHz, DMSO-$d_6$) δ (ppm): 11.21 (1H, s), 8.97 (3H, s), 7.82 (2H, d, J=1.5 Hz), 7.75 (1H, s), 7.03-7.26 (4H, m, J=7.5 Hz, 1.5 Hz), 5.88 (3H, s), 4.89 (1H, m), 4.41 (2H, d), 2.61 (2H, m, J=6.8 Hz), 2.34 (3H, s), 1.82 (6H, s), 1.29 (12H, d, J=6.8 Hz); $^{13}$C-NMR (101 MHz, DMSO-$d_6$) δ (ppm): 191.7, 165.2, 155.2, 154.3, 149.1, 143.2, 142.3, 141.5, 136.2, 134.6, 133.0, 130.3, 128.1, 127.6, 123.9, 119.1, 117.7, 115.9, 113.0, 110.1, 59.2, 30.5, 22.3, 20.3; MS (ESI) for (M+H)$^+$: 701.3.

Example 10

The preparation of compound J (Z)-8'-((1-(4-chlorophenyl)-5-oxo-3-vinyl-1H-pyrazol-4(5H)-ylidene)methyl)-1,1',6,6',7,7'-hexahydroxy-5,5'-diisopropyl-3,3'-dimethyl-[2,2'-binaphthalene]-8-carbaldehyde:

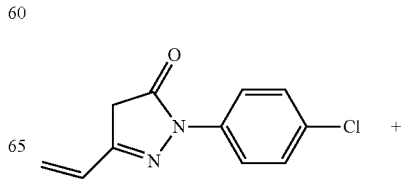

21

-continued

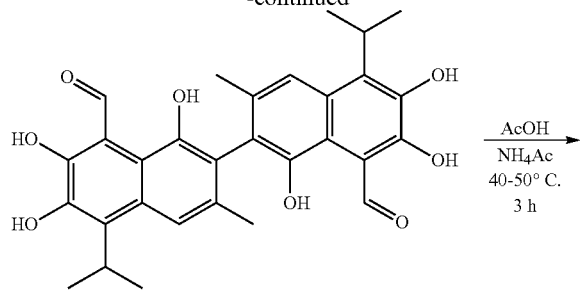

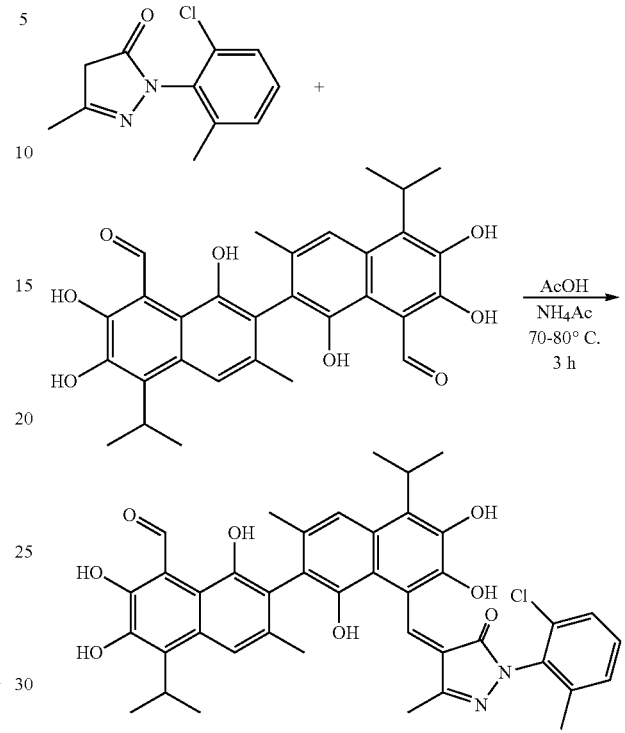

103.71 mg (0.2 mmol) of gossypol were dissolved in 25 mL of acetic acid in a 50 ml three-necked flask. 1.54 mg (0.02 mmol) of ammonium acetate was added to the gossypol solution under stirring and heating. 52.96 mg (0.24 mmol) of 1-(4-chlorophenyl)-3-ethenyl-1H-pyrazole-5-one in 8 mL acetic acid was slowly added to the mixture in the three-necked flask under stirring. The mixture was then heated to 40-50° C. for 3 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound J. The crude product was recrystallized from ethyl acetate and dried to obtain 118.39 mg (0.168 mmol) of compound J. The overall yield is 83.00%.

Compound J

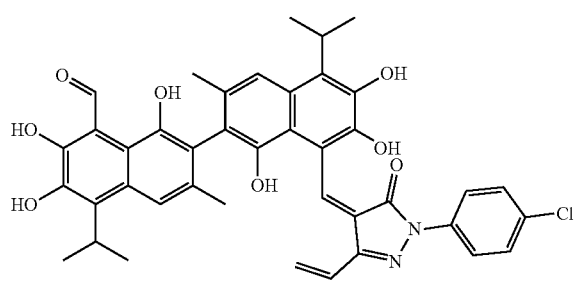

$^1$H-NMR (400 MHz, DMSO-$d_6$) δ (ppm): 11.20 (1H, s), 8.99 (3H, s), 7.98 (2H, d, J=1.5 Hz), 7.65 (1H, s), 7.33-7.56 (4H, m, J=7.5 Hz, 1.5 Hz), 5.78 (3H, s), 5.01 (1H, m), 4.61 (2H, d), 2.68 (2H, m, J=6.8 Hz), 1.92 (6H, s), 1.36 (12H, d, J=6.8 Hz); $^{13}$C-NMR (101 MHz, DMSO-$d_6$) δ (ppm): 192.7, 166.2, 156.2, 155.3, 150.1, 144.2, 143.3, 142.5, 135.2, 132.2, 130.3, 127.1, 126.6, 124.9, 118.1, 116.7, 114.9, 112.0, 109.1, 57.2, 31.5, 21.3, 19.3; MS (ESI) for (M+H)$^+$: 721.2.

Example 11

The preparation of compound K (Z)-8'-((1-(2-chloro-6-methylphenyl)-3-methyl-5-oxo-1H-pyrazol-4(5H)-ylidene)

22 methyl)-1,1',6,6',7,7'-hexahydroxy-5,5'-diisopropyl-3,3'-dimethyl-[2,2'-binaphthalene]-8-carbaldehyde:

103.71 mg (0.2 mmol) of gossypol were dissolved in 25 mL of acetic acid in a 50 ml three-necked flask. 1.54 mg (0.02 mmol) of ammonium acetate was added to the gossypol solution under stirring and heating. 53.44 mg (0.24 mmol) of 1-(2-chloro-6-methylphenyl)-3-methyl-1H-pyrazole-5-one in 5 mL acetic acid was slowly added to the mixture in the three-necked flask under stirring. The mixture was then heated to 70-80° C. for 3 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound K. The crude product was recrystallized from ethyl acetate and dried to obtain 98.36 mg (0.136 mmol) of compound K. The overall yield is 68.00%.

Compound K

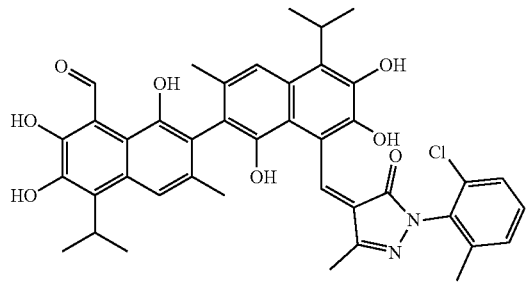

$^1$H-NMR (400 MHz, DMSO-$d_6$) δ (ppm): 11.23 (1H, s), 9.01 (3H, s), 7.81 (2H, s), 7.63 (1H, d, J=1.5 Hz), 7.51 (1H, s), 7.22, 7.13 (2H, m, J=7.5 Hz), 5.84 (3H, s), 2.85 (2H, m, J=6.8 Hz), 2.30 (6H, s), 2.21 (3H, s), 2.03 (3H, s), 1.44 (12H, d, J=6.8 Hz); $^{13}$C-NMR (101 MHz, DMSO-d$_6$) δ (ppm): 194.1, 165.6, 155.7, 154.1, 149.7, 143.5, 137.6, 134.7, 133.0, 131.2, 129.7, 127.4, 125.4, 122.9, 117.5, 116.7, 114.8, 113.9, 111.2, 110.2, 29.2, 25.6; MS (ESI) for (M+H)$^+$: 723.2

Example 12

The preparation of compound L (Z)-8'-((1-(2-chloro-6-methylphenyl)-5-oxo-3-vinyl-1H-pyrazol-4(5H)-ylidene)methyl)-1,1',6,6',7,7'-hexahydroxy-5,5'-diisopropyl-3,3'-dimethyl-[2,2'-binaphthalene]-8-carbaldehyde:

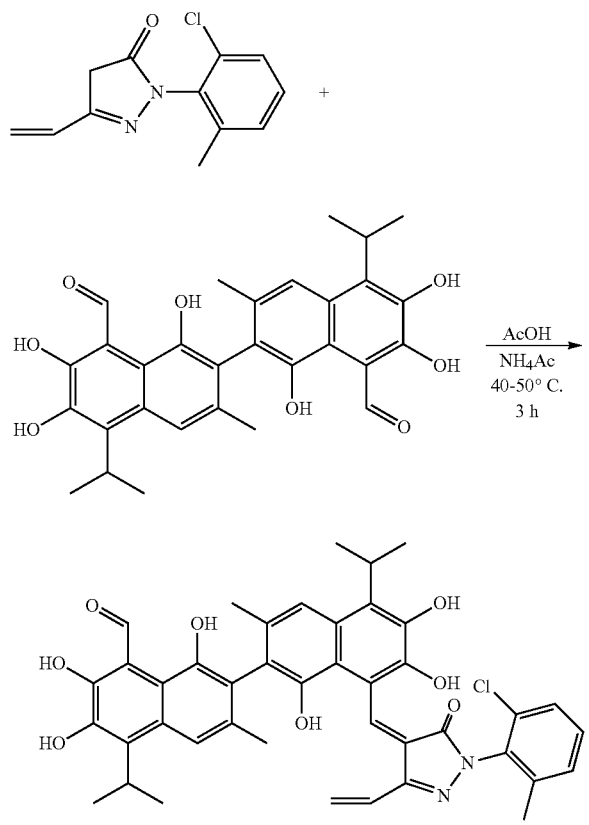

103.71 mg (0.2 mmol) of gossypol were dissolved in 25 mL of acetic acid in a 50 ml three-necked flask. 1.54 mg (0.02 mmol) of ammonium acetate was added to the gossypol solution under stirring and heating. 56.32 mg (0.24 mmol) of 1-(2-chloro-6-methylphenyl)-3-ethenyl-1H-pyrazole-5-one in 5 mL acetic acid was slowly added to the mixture in the three-necked flask under stirring. The mixture was then heated to 40-50° C. for 3 h. When TLC indicated that the reaction was complete, reaction was stopped. The reaction mixture was concentrated under reduced pressure. A small amount of water was added to the concentrated reaction mixture, and the mixture was then allowed to stand overnight for crystallization. The mixture was then filtered and washed with sodium bicarbonate solution to obtain crude compound L. The crude product was recrystallized from ethyl acetate and dried to obtain 89.70 mg (0.122 mmol) of compound L. The overall yield is 61.00%.

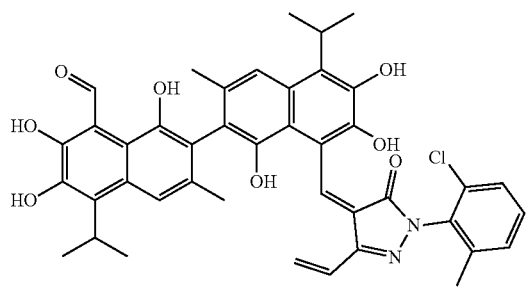

Compound L $^1$H-NMR (400 MHz, DMSO-d$_6$) δ (ppm): 11.15 (1H, s), 8.92 (3H, s), 7.92 (2H, s), 7.57 (1H, d, J=1.5 Hz), 7.45 (1H, s), 7.21, 7.16 (2H, m, J=7.5 Hz), 5.81 (3H, s), 5.15 (1H, m), 4.71 (2H, d), 2.82 (2H, m, J=6.8 Hz), 2.41 (6H, s), 2.07 (3H, s), 1.49 (12H, d, J=6.8 Hz); $^{13}$C-NMR (101 MHz, DMSO-d$_6$) δ (ppm): 191.2, 167.5, 156.6, 153.0, 147.5, 142.3, 141.6, 140.3, 136.4, 134.1, 130.2, 129.4, 128.0, 126.1, 125.2, 124.6, 122.9, 116.7, 114.8, 113.9, 112.1, 110.4, 59.3, 25.2, 22.0; MS (ESI) for (M+H)$^+$: 735.3.

Example 13

The Anti-Tumor Activity Test of the Compounds of the Present Invention

The compounds of the present invention were subjected to tumor cell proliferation inhibition test, and conventional MTT method was used.

Cell lines: human kidney cancer cells (A-498), human lung cancer cells (A-549), human brain astrocytoma cells (U-251). The culture medium was DMEM+15% NBS+ double antibody.

Sample solution preparation: after dissolving with DMSO (Merck), PBS (−) was added to obtain 100 μmol/L solution or homogeneous suspension. The solution was diluted with PBS (−) in DMSO to a final concentration of 0.1, 1, 10, 20, 40, 60, 80, 100 μmol/L.

Gossypol was used as control solution, prepared under the same condition.

Cell culture: adherent growth Tumor cells were cultured in 1640 medium containing 10% inactivated neonatal bovine serum and penicillin, streptomycin (1 million U/L), placed in carbon dioxide incubator at 37° C., 5% CO$_2$, and saturated humidity. Cells were treated serially passaged 2-3 times. The first culture was washed with PBS 2 times, and digested with trypsin. Fresh culture medium was added evenly, cells were adjusted to a appropriate concentration and transferred into a new culture flask. Cell in an exponential phase were chosen for the tests.

MTT Assay for Cell Viability and IC$_{50}$ Determination:

Experimental Principle: Living cells mitochondria in the dehydrogenase can reduce yellow MTT to water-insoluble blue-violet product MT (MTT formazan), deposited in the cells. The amount of production is proportional to the number of living cells. Dead cells do not reduce yellow MTT. DMSO can dissolve blue violet crystals, and the color depth is proportional to the amount contained, so the absorbance measured by the microplate reader can reflect the cell viability.

Methods: The exponential phase cells were digested and counted and seeded in 96-well plates at a density of 2×10$^4$/mL at 100 μl per well. After 24 hours of incubation, the cells to be tested were treated with 0.1, 1, 10, 20, 40, 60, 80, 100

μmol/L of the compounds. Each experimental group had 5 wells in each concentration, and the culture medium containing 0.4% DMSO was used as control. After 48 hours, the supernatant was discarded, and 100 μl of MTT ((2-(4,5-dimethyl-2-thiazolyl)-3,5-diphenyl-2H-tetrazole hydrobromide) (1 mg/mL) was added to each well. After another 4 hours, the supernatant was discarded, and 100 μl of DMSO was added to each well. After mixing, the absorbance was measured at 570 nm using a microplate reader. An $IC_{50}$ calculation software was used to determine the half inhibitory concentration ($IC_{50}$).

The test results are shown in Table 1. The compounds listed in the table correspond to the compounds described above.

TABLE 1

Half Inhibitory Concentration of Compounds on Different Tumor Cells $IC_{50}$ (unit: μmol/L)

| Compound | $IC_{50}$(μmol/L) | | |
|---|---|---|---|
| | A-498 | A-549 | U-251 |
| A | 11.43 ± 1.03 | 10.54 ± 0.92 | 10.41 ± 0.67 |
| B | 37.55 ± 2.23 | 78.42 ± 2.65 | 10.75 ± 0.61 |
| C | 25.33 ± 0.95 | >100 | >100 |
| D | 24.34 ± 0.91 | 36.89 ± 0.83 | >100 |
| E | 17.84 ± 0.95 | 26.72 ± 1.12 | 26.12 ± 1.80 |
| F | >100 | 65.87 ± 2.84 | 58.24 ± 2.10 |
| G | 26.51 ± 1.02 | 43.37 ± 1.21 | >100 |
| H | >100 | >100 | 78.65 ± 2.02 |
| I | 11.72 ± 0.65 | 18.14 ± 0.72 | 20.71 ± 0.84 |
| J | 13.84 ± 0.85 | 12.72 ± 1.12 | 26.23 ± 1.15 |
| K | >100 | >100 | 11.50 ± 1.32 |
| L | >100 | >100 | >100 |
| Gossypol | 11.29 ± 0.28 | 14.92 ± 0.64 | 20.15 ± 1.30 |

Compound A shows good antitumor activities in all three cell lines tested. Compound I, J, E and G also show good antitumor activities in different cell lines. The above experimental results show that the compounds of the present invention have good antitumor activities, and in particular, some edaravone-gossypol derivatives have superior antitumor activities than gossypol in some cell lines. These compounds can be used for the study of antitumor agents.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound with antitumor activities represented by formula I:

I

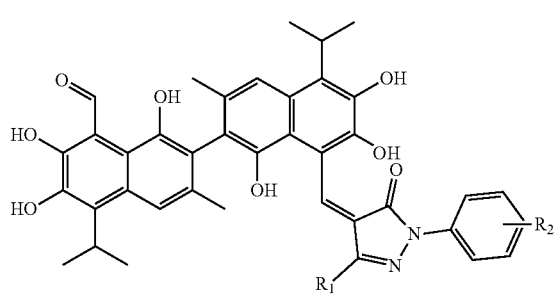

wherein $R_1$ is alkyl, alkoxy, or ethenyl; and $R_2$ is alkyl, alkoxy, or halogen.

2. The compound of claim 1, wherein the compound is selected from the group consisting of:

A

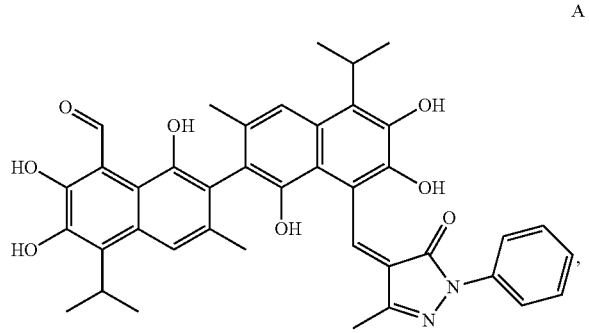

,

B

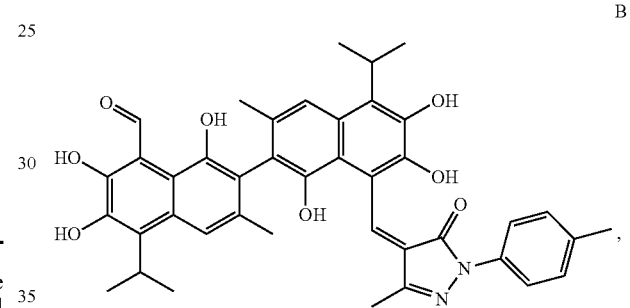

,

C

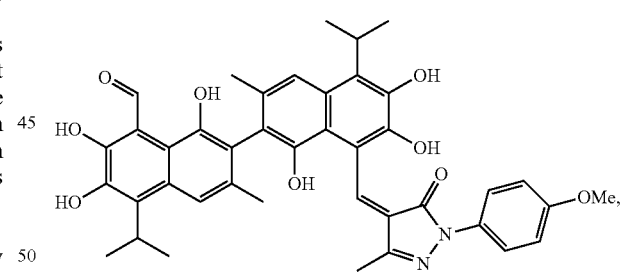

,

D

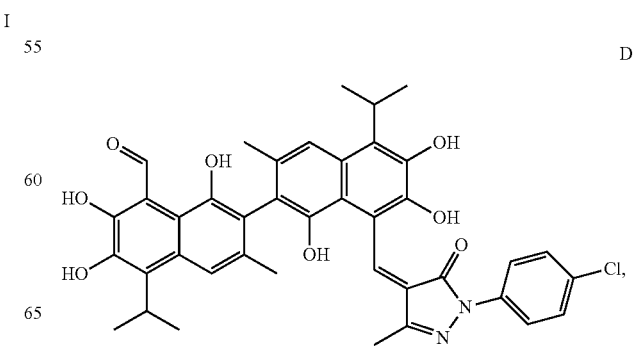

,

E
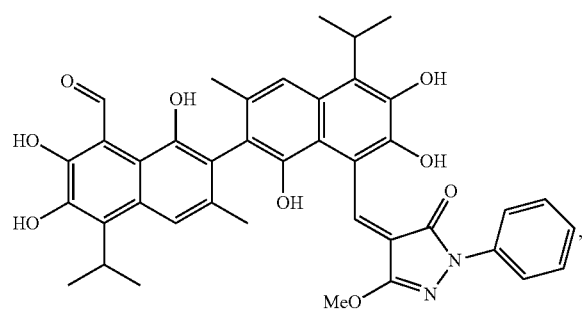
F
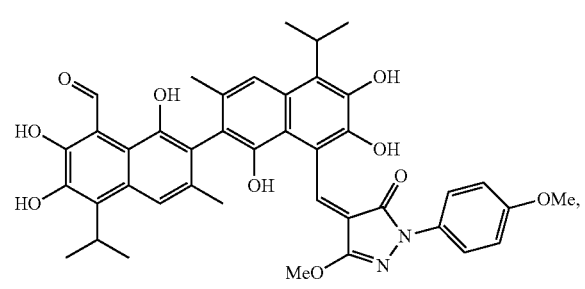
G
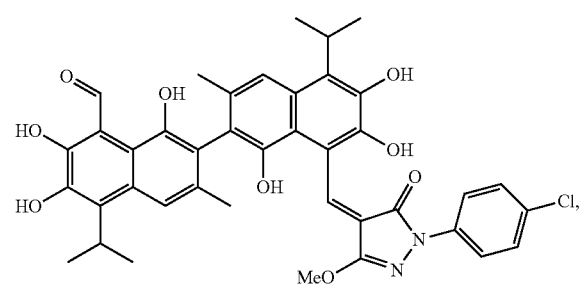
H
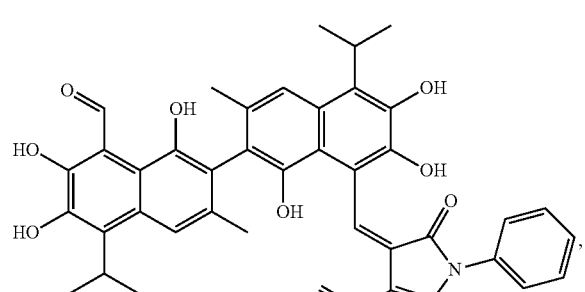
I
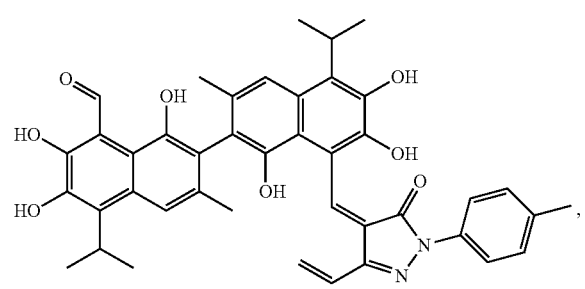
J
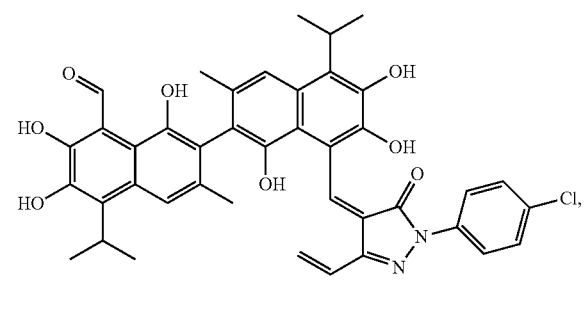
K
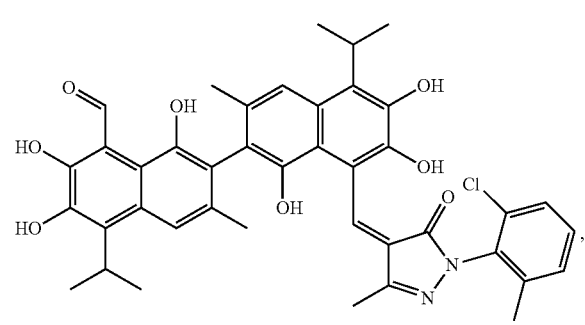
or
L
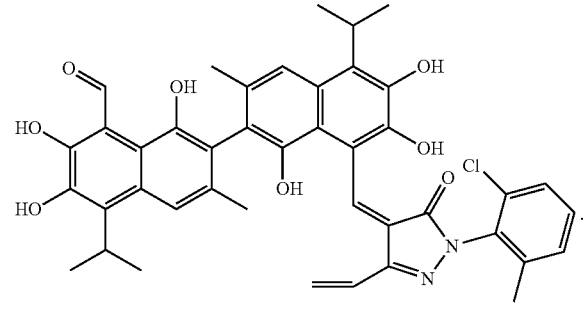
3. A method of preparing the compound of claim 1 comprising:
reacting a compound of formula A with a compound of formula B in an organic acid with ammonium acetate as a catalyst to obtain the compound of formula I,
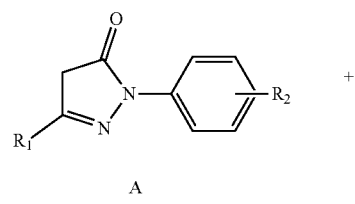
A

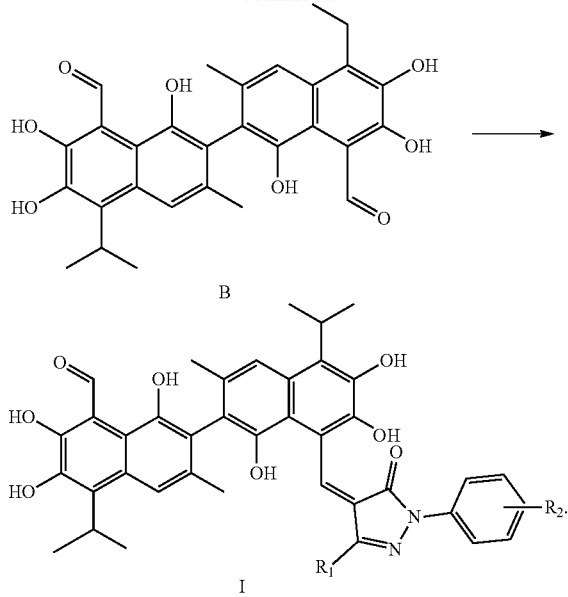

4. The method of claim 3, wherein the compound of formula A and the compound of formula B are heated at 40-80° C. for 2-5 hours.

5. The method of claim 4, wherein the compound of formula A and the compound of formula B are heated at 40-50° C. for 3 hours.

6. The method of claim 3, further comprising:

recrystallizing the compound of formula I in methanol or ethyl acetate.

7. The method of claim 3, wherein the organic acid is formic acid or acetic acid.

8. The method of claim 3, wherein a molar ratio of the compound B and the compound A is 1:1 to 1:1.5.

9. The method of claim 3, wherein the molar ratio of the compound B and the compound A is 1:1.2.

10. A method of using the compound of claim 1 in antitumor drug research, development, and application.

* * * * *